(12) United States Patent
Yamakawa et al.

(10) Patent No.: US 6,476,189 B1
(45) Date of Patent: Nov. 5, 2002

(54) ANTIBACTERIAL PEPTIDES AND ANTIBACTERIAL AGENTS CONTAINING SUCH PEPTIDES AS AN EFFECTIVE INGREDIENT

(75) Inventors: Minoru Yamakawa, Tsukuba (JP); Jun Ishibashi, Tsukuba (JP); Hisako Sakanaka, Ushiku (JP)

(73) Assignee: National Institute of Agrobiological Sciences, Tsukuba (JP)

( * ) Notice: Subject to any disclaimer, the term of this patent is extended or adjusted under 35 U.S.C. 154(b) by 0 days.

(21) Appl. No.: 09/510,751

(22) Filed: Feb. 22, 2000

Related U.S. Application Data (63) Continuation-in-part of application No. 09/372,386, filed on Aug. 11, 1999, now abandoned.

(30) Foreign Application Priority Data

Aug. 12, 1998 (JP) .......................................... 10-239435

(51) Int. Cl.⁷ .............................................. A61K 38/08
(52) U.S. Cl. ......................... 530/328; 530/330; 514/15
(58) Field of Search .................................. 530/330, 328

(56) References Cited

PUBLICATIONS

Walsh et al. J. Gen. Virol. (1998), 79(3), 479–487.*
Bowness et al. Eur. J. Immunol. (1994), 24(10), 2357–63.*

\* cited by examiner

*Primary Examiner*—Michael Borin
(74) *Attorney, Agent, or Firm*—Flynn, Thiel, Boutell & Tanis, P.C.

(57) ABSTRACT

An object of the present invention is to provide antibacterial peptides of high safety, improved antibacterial activity, wide antibacterial spectrum and lower molecular weight, and antibacterial agents containing such peptides as an effective ingredient, whose effects on in vivo immune system is decreased because of lower molecular weight thereof when they are given. To achieve this object, there are provided antibacterial peptides represented by the following formula:

$$X\text{-Ala-Ile-Arg-Lys-Arg-NH}_2 \qquad (1)$$

wherein X is a peptide in which one or more than two amino acid residues are linked by peptide linkage, and Arg-NH$_2$ means that a carboxyl group of Arg is amidated.

5 Claims, 3 Drawing Sheets

ANTIBACTERIAL PEPTIDES AND ANTIBACTERIAL AGENTS CONTAINING SUCH PEPTIDES AS AN EFFECTIVE INGREDIENT

This is a continuation-in-part of Ser. No. 09/372,386, filed Aug. 11, 1999, now abandoned.

BACKGROUND OF THE INVENTION

1. Field of the Invention

The present invention relates to antibacterial peptides and antibacterial agents containing such peptides as an effective ingredient.

2. Description of the Related Art

An intention of keeping our living environmnent dean and comfortable has been emphasized by sensational prevalence of pathogenic *Escherichia coli* O-157, etc. On the other hand, drug resistant microbes such as MRSA are developed as a result of excessive use of antibiotics, which would throw a shadow of feature uneasiness.

Various kinds of antibacterial agents including antibiotics have been provided and used not only for medical purposes but as a variety of so-called antibacterial goods.

Antibacterial peptides have been getting popular in the course of developing antibacterial agents.

The above mentioned peptides are present in semen or blood serum of mamals and is considered as one of the most noteworthy antibacterial ingredients because of a wider antibacterial spectrum and high safety, as well as infrequent appearance of drug resistant microbe by use thereof.

Existence of an antibacterial peptide derived from body fluid of insects has been known as such peptides. Further, it has been known that various kinds of antibacterial peptides are derived in body fluid of insects when bacteria or different blood corpuscles are inoculated to insects or stimulation is given to a body surface thereof by wounding, etc.

For example, an antibacterial active peptide has been identified, which is derived from body fluid of a larval *Zophobas atratus*, an insect of Tenebriodae (see, J. Biol. Chem., vol. 266, pp. 24,524 to 24,525, 1991).

Further, physical and chemical properties of an antibacterial peptide named as Coleoptericin have been investigated.

On the other hand, an antibacterial peptide of cecropin group which is derived from body liquid of larval *Hyalophora cecropia*, an insect of Lepidoptera, itself and physical and chemical properties thereof have been found and investigated.

Antibacterial peptides derived from these insects have a wide antibacterial spectrum and accordingly are considered to bear important relation to biological defense of such insects which are lack of antibody forming ability.

One of problems associated with these antibacterial peptides includes antigenicity. Each of antibacterial peptides has not so low molecular weight and can be antigen in the body when they are vascularly administered as an antibacterial agent.

Because of the wide but somewhat biased antibacterial spectrum, there are not necessarily provided antibacterial peptides which are sufficiently effective to both Gram-positive and Gram-negative bacteria.

Further, there is no gainsaying possible development of some cytotoxicity when these insect-derived antibacterial peptides are given to mammals.

SUMMARY OF THE INVENTION

Accordingly, it is an object of the present invention to provide antibacterial measure by use of antibacterial peptides which overcome conventional problems as described above.

In order to solve conventional problems, structure and functions of an antibacterial peptide derived from insects of Lepidoptera such as Scarabaeidae, Tenebriodae, etc., especially *Oryctes rhinoceros* which is an insect of Eophileurus chinensis of Scarabaeidae have been investigated as an insect-derived peptide by the present inventor.

It is known that an antibacterial peptide is induced in body liquid of larva *Oryctes rhinoceros* when stimulated by, for example, wounding. Using cDNA of larva *Oryctes rhinoceros*, its nucleotide sequence encoding an antibacterial peptide (hereinafter referred to as natural antibacterial peptide gene) was identified.

Then, amino acid sequence of an antibacterial peptide derived from *Oryctes rhinoceros* (hereinafter referred to as natural antibacterial peptide unless otherwise noted) was estimated from the nucleotide sequence thus identified. Development of novel antibacterial peptides has been done on the basis of information of such amino acid sequence.

[1] Nucleotide sequence identification of natural antibacterial peptide cDNA

The nucleotide sequence of natural antibacterial peptide cDNA was identified by a conventionally known method as in the following.

(1) The natural antibacterial peptide was extracted from larva *Oryctes rhinoceros* and purified to identify N-terminal amino acid sequence thereof Based on the amino acid sequence, a degenerate primer was synthesized. In addition, another degenerate primer was also synthesized based on the conserved amino acid sequence of the C-terminal region of the insect antibacterial peptide family designated defensive.

(2) Using these oligonucleotides as primers, a portion which would code the antibacterial peptide cDNA, was subjected to manipulation of gene amplification (PCR method).

(3) The nucleotide sequence of PCR product was determined.

In order to identify N-terminus of the natural antibacterial peptide in the above mentioned process (1), separation and purification of the natural antibacterial peptide from larva *Oryctes rhinoceros* were carried out as in the following.

Ten of the third instar larvae of *Oryctes rhinoceros* were kept on ice for several minutes to slow down their movement and wounded by piercing a hypodermic needle. The thus wounded larvae were kept in a breeding box with leaf mold for 24 to 48 hours at a temperature of 25° C.

After cutting legs of wounded larva *Oryctes rhinoceros*, drops of their body liquid was squeezed and collected in a tube on ice by pressing abdomen thereof. As a result, about 1.5 ml of body liquid was obtained from each larva.

After the above mentioned body liquid was subjected to centrifugal separation (39,000× g) for 50 minutes, a blood corpuscle component was removed and the supernatant thus obtained was kept at a temperature of−20° C. Then, 15 ml of the supernatant was applied to Sep-Pak C18-cartridge (available from Waters Associates Co., Ltd.) which had been equilibrated with a solvent A containing 20% of acetonitrile, followed by washing the column with the solvent A, to elute an antibacterially active substance (active fraction) with a 20%-acetonitrile/0.05%-trifluoroacetic acid solution.

The active fraction was freeze-dried to remove acetonitrile and form a dried powder, which was dissolved in a 0.05%-trifluoroacetic acid solution to apply to Resource RPC Column (1 ml; available from Pharmacia Co., Ltd.) which had been equilibrated with a 0.05%-heptafluorobutytir acid (HFBA) solution.

The column was washed with the 5%-HFBA solution, followed by gradient elution under a condition of 0% to 20%-acetonitrile/0.05%-trifluoroacetic acid solution for 1.25 minutes; similarly a 20% to 40%-solution for 10 minutes and a 40% to 100%-solution for 1.25 minutes. It was observed that an 38 to 40%-acetonitrile fraction is antibacterially active.

The antibacterial activity was observed as in the following.

To 0.99 ml of a bouillon medium prepared by dissolving 1 g of beef extract (available from Difco Co., Ltd), 2 g of Bacto-peptone (available from Difco Co., Ltd.) and 1 g of NaCl in 200 ml of water, 10 µl of bacteria suspension prepared by culturing *Staphylococcus aureus* in bouillon medium overnight was added and cultured up to period of logarithmic multiplication.

To bouillon-agar medium prepared by adding 1.5% by weight of agar to the bouillon medium, 200 µl of the thus obtained culture solution was added and poured to a laboratory dish to gelate it. Then, a well of 2 mm in diameter was formed on the gelled bouillon-agar medium by means of a gel puncher (available from Parmacia Co., Ltd.). Five µl of 38 to 40%-acetonitrile fraction (sample) dissolved in water was poured into the well and cultured overnight at a temperature of 37° C. to observe a hollow formed thereon.

A procedure described above was repeated similarly.

The active fraction was further freeze-dried to remove acetonitrile and form a dried powder, which was dissolved in the solvent A to apply to a column (3.2×30 mm, µ RPC C2/C18 PC3.2/3 column, available from Pharmacia Co., Ltd.). After the column was washed by the solvent A, elution was carried out under a mild gradient condition of 20% to 40%-acetonitrile/0.05%-trifluoroacetic acid for 40 minutes. It was observed that an 23 to 24%-acetonitrile fraction is antibacterially active.

The thus obtained fraction of natural antibacterial peptide was applied to a reversed column (2.1×100 mm, µ RPC C2/C18 SC2.1/10, available from Pharmacia Co., Ltd.) which had been equilibrated with the solvent A. The reversed column was connected to SMART system (available from Pharmacia Co., Ltd.) and washed by the solvent A, followed by elution under a mild gradient condition 0% to 20%-acetonitrile/0.05%-trifluoroacetic acid for 5 minutes; 20% to 40% for 40 minutes and 40% to 100% for 5 minutes.

Figure 1:
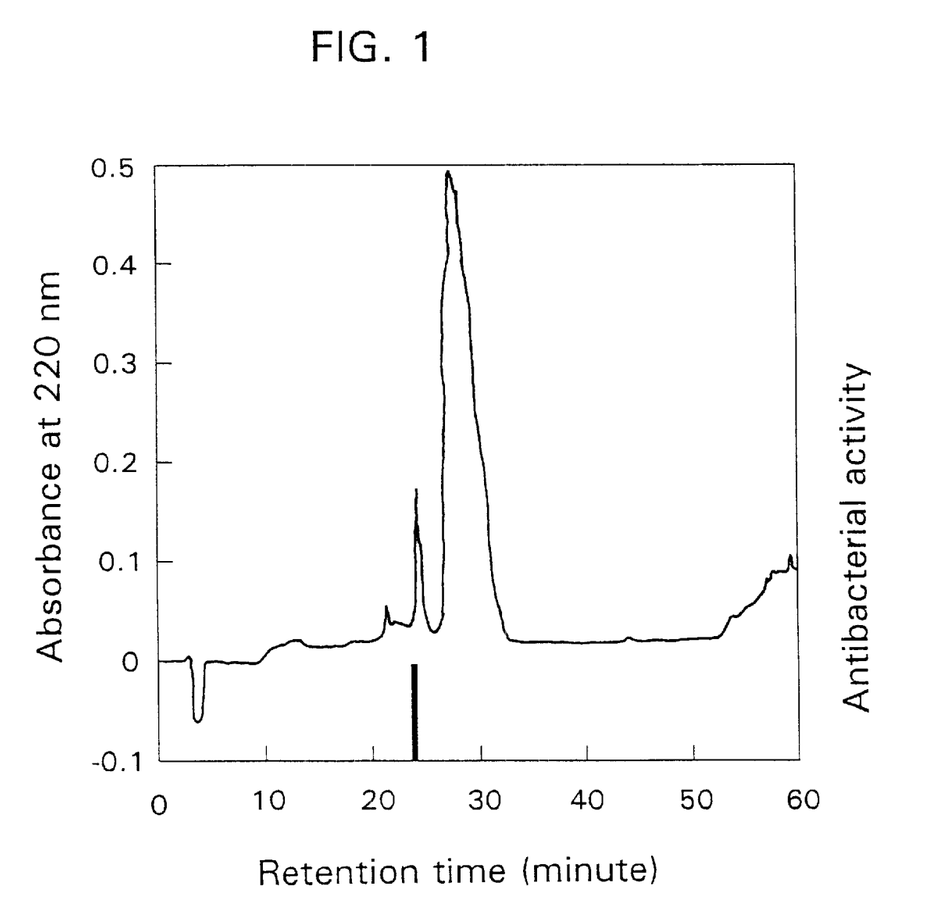
FIG. 1 is a reversed phase column chromatogram (SMART system) of a natural antibacterial peptide which shows antibacterial activity of finally purified profile thereof against *Staphylococcus aureus*.
Figure 2:
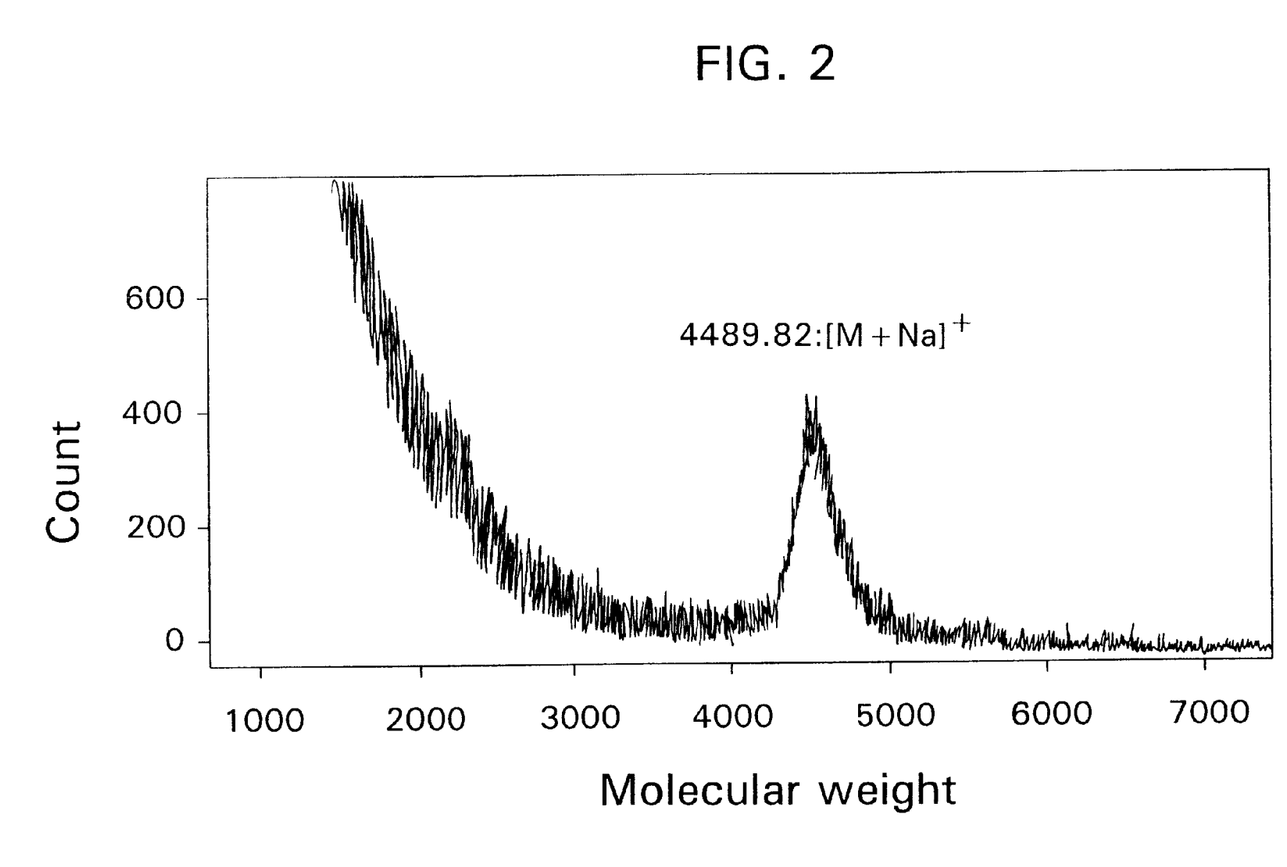
FIG. 2 is a mass spectrogram (MALDI-TOF-MS) of a natural antibacterial peptide.

The thus obtained eluent was fractionated to each 200 µl-fraction, which was then freeze-dried to observe the antibacterial activity one after the other. The antibacterial activity was eluted as a single peak compatible with that of protein as shown in FIG. 1. Mass spectrometry (MALDI-TOF-MS) of the antibacterially active fraction showed a single molecular weight of 4,489 (M+Na) as shown in FIG. 2.

The thus obtained fraction, which was considered as the natural antibacterial peptide, was subjected to Edman degradation to determine the amino acid sequence. It was found that the sequence of 15 PTH-amino acid residues (sequence No. 1) which would correspond to a N-terminus of the natural antibacterial peptide is as in the following:

Leu Thr Cys Asp Leu Leu Ser Phe Glu Ala Lys Gly Phe Ala Ala
      1            5              10           15

Figure 3:
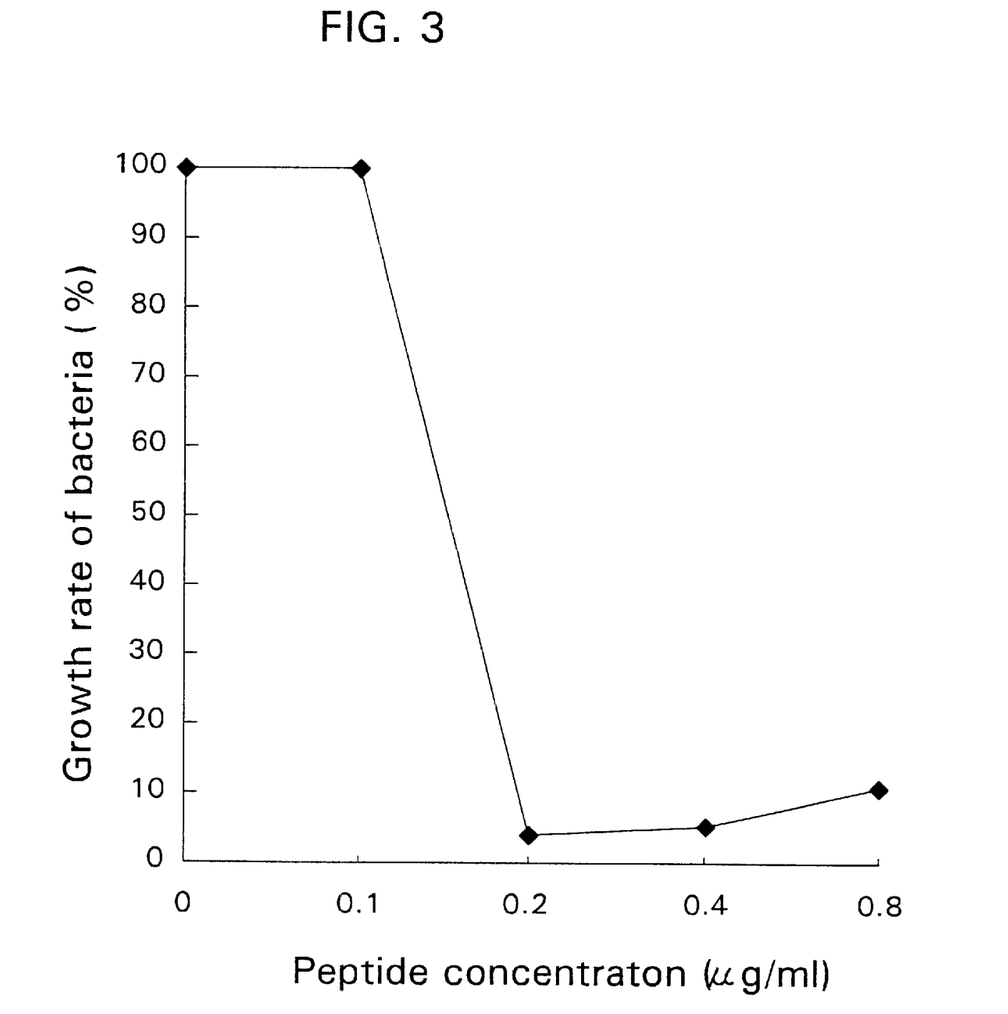
FIG. 3 is a graph which shows the effect of increased concentration of a natural antibacterial peptide on the growth of *Staphylococcus aureus*.

The antibacterial activity of the present natural antibacterial peptide was determined by changing an amount of protein from 0 to 0.8 in 50 µl of test solution. The result is shown in FIG. 3, from which it is confirmed that the antibacterial activity of this peptide is clearly effective to *Staphylococcus aureus*. Further, the natural antibacterial peptide was subjected to a heat treatment at a temperature of 100° C. for 5 to 10 minutes, thereby the initial antibacterial activity being kept.

A degenerate oligonucleotide primer was synthesized based on the amino acid sequence of the N-terminal region of natural antibacterial peptide following the procedure described above (I).

On the other hand, another degenerate primer was synthesized based on the amino acid sequence of the conserved C-terminal region of the closely related antibacterial peptide family.

The first strand cDNA was prepared using a restricted enzyme Not I site-added primer with fat body mRNA of *Escherichia coli*-infected third instar larva *Oryctes rhinoceros* as a template, to which PCR-gene amplification was carried out using the above mentioned PCR primer. As a result, an amplified gene product of about 120 bp in length was obtained.

Nucleotide sequence of the amplified gene product was determined, while a primer was further prepared according to the nucleotide sequence and subjected to the PCR-amplification between a complementary primer to the restricted enzyme Not I site which was used to prepare the first strand cDNA. As a result, nucleotide sequence of the amplified gene product at the 3'-terminal side was elucidated.

Further, the first strand cDNA was prepared using the primer based on the base sequence thus identified with fat body mRNA of *Escherchia coli*-infected third instar larva *Oryctes rhinoceros* as a template. Then, poly C sequence was added to the cDNA at the 5'-terminal, which was used as a template for a primer having poly G sequence. Using thus prepared primer and the above mentioned primer, which was prepared according to the identified nucleotide sequence, as PCR primers, the PCR amplification was conducted. Nucleotide sequence of the amplified gene product at the 5'-side was determined.

Nucleotide sequence information thus clarified one after the other were put together to confirm cDNA nucleotide sequence which is capable of coding the natural antibacterial peptide derived from *Oryctes rhinoceros* (See, Sequence No. 2). The amino acid sequence estimated from this nucleotide sequence is also shown in Sequence No. 2.

DNA having the Sequence No. 2 was integrated into a congenic vector (pCR 2-1; available from Invitrogen Co., Ltd.) to transform *Escherichia coli* JM 109. The transformant has been deposited to the National Institute of Bioscience and Human-Technology (NIBH) as pCROAD (Dpodition No. FERM P-16,800).

As a result of comparison of the estimated amino acid sequence represented by the Sequence No. 2 and that of the natural antibacterial peptide at the N-terminus in the Sequence No. 1, it was confirmed that amino acid residues from the first Met to the 36th Arg are extracellularly secreting signal peptide and propeptide, while those residues from the 37th Leu to Arg just prior to the last codon are maturated natural antibacterial peptide which actually exhibits antibacterial activity.

The natural antibacterial peptide, whose amino acid sequence has been confirmed as described above, comprises 43 amino acid residues and exhibits high antibacterial activity.

[2] Preparation of novel peptide

Size of the above mentioned peptide comprising 43 amino acid residues, however, is large enough to function as an immunogen in an in vivo immune system. That is, it is undesirable that the natural antibacterial peptide might activate the immune system when such a peptide is given to an organism.

Further, the natural antibacterial peptide has an antibacterial spectrum only against Gram-positive bacteria but exhibits little activity against Gram-negative bacteria.

Accordingly, the present inventor has investigated the amino acid sequence of the natural antibacterial peptide in detail and found that residues from the 62nd Ala to the 69th Ala of the above mentioned amino acid sequence are in charge of the antibacterial activity. It is thus considered that activation of the host immune system caused by the natural antibacterial peptide can be reduced when an active center portion thereof is used as an antibacterial agent.

It is also considered that a change in amino acid sequence around the active center portion may improve in an antibacterial spectrum not only to Gram-positive but Gram-negative bacteria.

It is finally found that certain peptide which comprises specific amino acid sequence having amidated C-terminus as a core portion has high antibacterial activity against both Gram-positive and Gram-negative bacteria, although molecular size thereof is relatively small. On the basis of this information, the present invention has been completed.

The present invention provides antibacterial peptides represented by the following formula:

$$X\text{-Ala-Ile-Arg-Lys-Arg-NH}_2 \tag{1}$$

wherein X is peptide in which one or more than two amino acid residues are linked by peptide linkage, and Arg-NH$_2$ means that a carboxyl group of Arg is amidated.

There are also provided antibacterial agents containing the antibacterial peptide as an effective ingredient and, in particular, edible antibacterial agents which can be taken in digestive tracts.

DESCRIPTION OF THE PREFERRED EMBODIMENT

The present invention will be further detailed in the following preferred embodiment.

Antibacterial peptides of the present invention are represented by the following formula:

$$X\text{-Ala-Ile-Arg-Lys-Arg-NH}_2 \tag{1}$$

wherein X is peptide in which one or more than two amino acid residues are linked by peptide linkage, and Arg-NH2 means that a carboxyl group of Arg is amidated.

The present antibacterial peptides include L- and D-optical isomers.

A portion of "Ala-Ile-Arg-Lys-Arg" is essential structure for the antibacterial peptides to exhibit antibacterial activity or, in other words, desired activity is hardly expected without this portion.

As described above, Arg- NH$_2$ means that a carboxyl group thereof is amidated. Such an amidation is also an essential requirement for the antibacterial peptides of the present invention to exhibit their antibacterial activity sufficiently. If a certain peptide comprises the structure "Ala-Ile-Arg-Lys-Arg" at the C-terminus, it is difficult to obtain desired antibacterial activity.

As described above, X represents peptides in which one or more than two amino acid residues are linked by peptide linkage and is not limited to a specific peptide unless otherwise the present antibacterial peptides exhibit no activity. Number of amino acid residues contained in X is preferably more than three, more preferably three or four, and the most preferably four from a standpoint of the "antibacterial activity". When the number of amino acid residues is two or less, the antibacterial activity tends to decrease.

As number of amino acid residues contained in X is preferably three or four, the size or molecular weight is quite small as a peptide of specific functions Such a low molecular peptide is seldom affected by an in vivo immune system, which indicates that the present antibacterial peptides are highly effective from an "immunogen" standpoint.

When number of amino acid residues of X is four, the sequence of X is represented by the following formula:

$$\text{Ala-Xaa}^1\text{-Xaa}^2\text{-Leu} \tag{II}$$

wherein Xaa$^1$ and Xaa$^2$ may be the same or different and are an amino acid residue other than acidic one. Such structure preferably exhibits wider and higher antibacterial activity An amino acid residue to be excluded from those residues of Xaa$^1$ and Xaa$^2$ are, for example, aspartic and glutamic residues.

The peptide X represented by the formula (II) includes a practical combination of amino acid residues such as Ala-Leu-Arg-Leu, Ala-Leu-Leu-Leu, Ala-Trp-Leu-Leu, Ala-Leu-Try-Leu or Ala-Leu-Trp-Leu.

The present antibacterial peptides may be prepared by generally known methods for preparing peptides. Such well known methods include solid phase synthesis, liquid phase synthesis, etc. A commercially available automatic peptide synthesizing system may also be used as a matter of course.

Amidation of a carboxyl group of arginine (Arg) located at the C-terminus of the present antibacterial peptide may be conducted by generally known methods. For example, such a carboxyl group of Arg may be amidated by using a solid resin carrier on which an amino group is introduced as a solid phase carrier for the above mentioned solid phase peptide synthesis.

The present antibacterial peptides may be prepared easily in the above mentioned manner. The present antibacterial peptides comprise a modified short chain and thus, may be prepared by completely chemical synthesis without relying on a gene engineering technique in which, for example, a desired peptide-coding gene is prepared and then gene expression thereof is conducted in a suitable host.

Although a method for preparing the present antibacterial peptides is quite easy as described above, it is a striking characteristic that the thus prepared peptides exhibit wide antibacterial activity against both Gram-positive and Gram-negative bacteria. As a mater of course, gene engineering may be employed in the present invention as an optional technique.

The present antibacterial peptides may be used as an active ingredient to prepare useful antibiotics (hereinafter referred to as the present antibacterial agents).

The present antibacterial agents may be prepared as a medicinal composition by blending the present antibacterial peptides and medicinal carriers.

The medicinal carriers may be properly selected from known products depending on a practical form to be prepared. Such carriers include shaping or diluting materials such as filler, extender, binder, humidifier, disintegrator, surfactant, etc.

The present antibacterial agents are not limited to a specific medicinal form so far as the desired antibacterial activity is effectively exhibited and may either be in forms of solid such as tablet, powder and pill or an injection such as liquid, suspension, emulsion.

Dose of the present peptides contained in the antibacterial agents should be properly controlled by kinds of dosage forms, diseases or symptoms to be treated, etc., and is not limited to a specific amount.

As the present antibacterial peptides comprise essential amino acid, it is considered that toxicity thereof to human is seldom observed through oral uptake.

The present antibacterial peptides may be used for food or feed for human or animal. That is, these peptides are useful as food and feed additives.

EXAMPLE

The following example is set forth to further describe the present invention and is not intended to restrict it.

Preparation of the Present Antibacterial Peptides

Using a commercially available peptide synthesizing system "Peptide Synthesizer 9050 plus" (available from Per-Septive Biosystems Co., Ltd.), the present peptides (1) to (5) were prepared as in the following. "Fmoc PAL-Polyethylene (PEG-PS) resin" was used as a solid phase carrier to amidate the C-terminus (amino acid to be amidated was Fmoc-L-amino acid).

present peptide (1): Ala-Leu-Arg-Leu-Ala-Ile-Arg-Lys-Arg-NH$_2$ sequence No. 3 present peptide (2): Ala-Leu-Leu-Leu-Ala-Ile-Arg-Lys-Arg-NH$_2$ sequence No. 4 present peptide (3): Ala-Trp-Leu-Leu-Ala-Ile-Arg-Lys-Arg-NH$_2$ sequence No. 5 present peptide (4): Ala-Leu-Tyr-Leu-Ala-Ile-Arg-Lys-Arg-NH$_2$ sequence No. 6 present peptide (5): Ala-Leu-Trp-Leu-Ala-Ile-Arg-Lys-Arg-NH$_2$ sequence No. 7

Test Example (Effectiveness)

Minimum Inhibitory Concentration (MIC) of these antibacterial peptides (1) to (5) against *Staphylococcus aureus*, methicillin resistant *Staphylococcus aureus* (MRSA), *Escherichia coli* and *Pseudomonas aeruginosa* was determined. The result is shown in Table 1.

TABLE 1

| antibacterial peptides | S. aureus | MRSA | E. coli | P. aeruginosa |
|---|---|---|---|---|
| present peptide (1) | 5 | — | 4 | >15 |
| present peptide (2) | 4 | 40 | 6 | 4 |
| present peptide (3) | 3 | 25 | 5 | 4 |
| present peptide (4) | 2 | 30 | 4 | 4 |
| present peptide (5) | 4 | 40 | 10 | 10 |

(MIC: µg/ml)

The result clearly shows that the present peptides exhibit high antibacterial activity and also wide antibacterial spectrum.

Test Example (Safety)

Peritoneal injection toxicity of the present antibacterial peptides (1) to (5) was tested to determine LD$_{50}$ to mice. As a result, LD$_{50}$ of these peptides was higher than 150 mg/kg, which demonstrated that toxicity thereof to warm-blooded animals is quite low.

Example of Preparation

Exemplary preparations containing the present antibacterial peptides will be described in the following.

(1) Injection

Each of the present antibacterial peptides (1) to (5) in an amount of 100 mg was dissolved in 100 ml of physiological saline solution, respectively, which was then charged in 2.5 ml-ampoules and sealed under a sterile condition to prepare injection.

(2) Granule

Each of the present antibacterial peptides (1) to (5) in an amount of 500 mg was mixed with 50 mg of crystalline cellulose and 450 mg of lactose, followed by blending together with 1 ml of an ethanol- water mixture. The thus obtained blend was granulated in a conventional manner to form granules.

Effect of the Invention

The present invention provides antibacterial peptides of high safety, improved antibacterial activity, wide antibacterial spectrum and lower molecular weight, and antibacterial agents containing such peptides as an effective ingredient, whose effects on in vivo immune system is decreased because of lower molecular weight thereof when they are given.

What is claimed is:

1. Antibacterial peptides represented by the following formula:

$$\text{X-Ala-Ile-Arg-Lys-Arg-NH}_2 \quad (I)$$

in which X is Ala-Xaa$^1$-Xaa$^2$-Leu, wherein Xaa$^1$ and Xaa$^2$ are the same or different amino acid residue, other than an acidic amino acid residue, and Arg-NH$_2$ means that a carboxyl group of Arg is amidated.

2. Antibacterial peptides represented by the following formula:

$$\text{X-Ala-Ile-Arg-Lys-Arg-NH}_2 \quad (I)$$

where X is a peptide of an amino acid sequence selected from the group consisting of Ala-Leu-Arg-Leu, Ala-Leu-Leu-Leu, Ala-Trp-Leu-Leu, Ala-Leu-Tyr-Leu and Ala-Leu-Trp-Leu and Arg-NH$_2$ means that a carboxyl group of Arg is amidated.

3. An antibacterial agent containing an antibacterial peptide represented by the following formula:

$$\text{X-Ala-Ile-Arg-Lys-Arg-NH}_2 \quad (I)$$

in which X is Ala-Xaa$^1$-Xaa$^2$-Leu, wherein Xaa$^1$ and Xaa$^2$ are the same or different amino acid residue, other than an acidic amino acid residue, and Arg-NH$_2$ means that a carboxyl group of Arg is amidated.

4. The antibacterial agent of claim 3, wherein X is a peptide of an amino acid sequence selected from the group consisting of Ala-Leu-Arg-Leu, Ala-Leu-Leu-Leu, Ala-Trp-Leu-Leu, Ala-Leu-Tyn-Leu and Ala-Leu-Trp-Leu.

5. The antibacterial agent of claim 4, wherein said antibacterial agent is edible.

* * * * *

SEQUENCE LISTING (1) GENERAL INFORMATION:

(iii) NUMBER OF SEQUENCES:7

(2) INFORMATION FOR SEQ ID NO:1:

(i) SEQUENCE CHARACTERISTICS:
      (A) LENGTH:15
      (B) TYPE:amino acid
      (C) STRANDEDNESS:
      (D) TOPOLOGY:unknown    (ii) MOLECULE TYPE:peptide    (v) FRAGMENT TYPE:N-terminal    (vi) ORIGINAL SOURCE:
      (A) ORGANISM:Oryctes rhinoceros    (xi) SEQUENCE DESCRIPTION: SEQ ID NO:1:

```
Leu Thr Cys Asp Leu Leu Ser Phe Glu Ala Lys Gly Phe Ala Ala
  1               5                  10                  15
```

(2) INFORMATION FOR SEQ ID NO: 2:

(i) SEQUENCE CHARACTERISTICS:
      (A) LENGTH:316
      (B) TYPE:nucleic acid
      (C) STRANDEDNESS: double strand
      (D) TOPOLOGY:linear    (ii) MOLECULE TYPE:cDNA    (xi) SEQUENCE DESCRIPTION: SEQ ID NO:2:

```
TGACTCATAC AACAAATCGC AGAGCTTACG ACAAG ATG TCG AGG TTT ATC GTA          53
                                       Met Ser Arg Phe Ile Val
                                         1               5

TTT GCT TTC ATC GTA GCC ATG TGC ATT GCA CAC AGT TTA GCT GCG CCA        101
Phe Ala Phe Ile Val Ala Met Cys Ile Ala His Ser Leu Ala Ala Pro
 10              15                  20

GCA CCA GAA GCG CTT GAA GCT AGC GTC ATA AGA CAA AAG AGA CTG ACG        149
Ala Pro Glu Ala Leu Glu Ala Ser Val Ile Arg Gln Lys Arg Leu Thr
 25              30                  35

TGC GAT CTT CTG AGT TTC GAA GCT AAG GGT TTT GCT GCC AAT CAC AGC        197
Cys Asp Leu Leu Ser Phe Glu Ala Lys Gly Phe Ala Ala Asn His Ser
 40              45                  50

CTG TGC GCT GCT CAT TGC CTA GCT ATT GGA CGC AAA GGT GGT GCT TGT        245
Leu Cys Ala Ala His Cys Leu Ala Ile Gly Arg Lys Gly Gly Ala Cys
 55              60                  65                      70

CAA AAT GGG GTT TGT GTG TGC AGA AGA TAG ATCTGTTATA GTTTTTTTTT         295
Gln Asn Gly Val Cys Val Cys Arg Arg
 75

AATAGATCAT TTTTTTTATT T                                                316
```

(2) INFORMATION FOR SEQ ID NO:3:

(i) SEQUENCE CHARACTERISTICS:
      (A) LENGTH:9
      (B) TYPE:amino acid
      (C) STRANDEDNESS:
      (D) TOPOLOGY:linear    (ii) MOLECULE TYPE:peptide    (xi) SEQUENCE DESCRIPTION: SEQ ID NO:3:

Ala Leu Arg Leu Ala Ile Arg Lys Arg

```
1              5

(2) INFORMATION FOR SEQ ID NO:4:

(i) SEQUENCE CHARACTERISTICS:
        (A) LENGTH:9
        (B) TYPE:amino acid
        (C) STRANDEDNESS:
        (D) TOPOLOGY:linear (ii) MOLECULE TYPE:peptide (xi) SEQUENCE DESCRIPTION:  SEQ ID NO:4:

Ala Leu Leu Leu Ala Ile Arg Lys Arg
1              5

(2) INFORMATION FOR SEQ ID NO:5:

(i) SEQUENCE CHARACTERISTICS:
        (A) LENGTH:9
        (B) TYPE:amino acid
        (C) STRANDEDNESS:
        (D) TOPOLOGY:linear (ii) MOLECULE TYPE:peptide (xi) SEQUENCE DESCRIPTION:  SEQ ID NO:5:

Ala Trp Leu Leu Ala Ile Arg Lys Arg
1              5

(2) INFORMATION FOR SEQ ID NO:6:

(i) SEQUENCE CHARACTERISTICS:
        (A) LENGTH:9
        (B) TYPE:amino acid
        (C) STRANDEDNESS:
        (D) TOPOLOGY:linear (ii) MOLECULE TYPE:peptide (xi) SEQUENCE DESCRIPTION:  SEQ ID NO:6:

Ala Leu Tyr Leu Ala Ile Arg Lys Arg
1              5

(2) INFORMATION FOR SEQ ID NO:7:

(i) SEQUENCE CHARACTERISTICS:
        (A) LENGTH:9
        (B) TYPE:amino acid
        (C) STRANDEDNESS:
        (D) TOPOLOGY:linear (ii) MOLECULE TYPE:peptide (xi) SEQUENCE DESCRIPTION:  SEQ ID NO:7:

Ala Leu Trp Leu Ala Ile Arg Lys Arg
1              5
```